United States Patent [19]

Daire

[11] Patent Number: 6,103,945

[45] Date of Patent: *Aug. 15, 2000

[54] PROCESS FOR CONVERTING THE LOW-BOILING BY-PRODUCTS FORMED DURING THE THERMAL CRACKING OF 1,2-DICHLOROETHANE

[75] Inventor: Sylvie Daire, Chateauneuf-les-Martigues, France

[73] Assignee: Elf Atochem S.A., France

[ * ] Notice: This patent issued on a continued prosecution application filed under 37 CFR 1.53(d), and is subject to the twenty year patent term provisions of 35 U.S.C. 154(a)(2).

[21] Appl. No.: 08/816,994

[22] Filed: Mar. 14, 1997

[30] Foreign Application Priority Data

Mar. 14, 1996 [FR] France .................................. 96 03208

[51] Int. Cl.⁷ ............................ C07C 17/25; C07C 17/38
[52] U.S. Cl. .......................... 570/220; 570/219; 570/238
[58] Field of Search .................... 570/220, 219, 570/238

[56] References Cited

FOREIGN PATENT DOCUMENTS

| 2 038 347 | 1/1971 | France . | |
|---|---|---|---|
| 2063188 | 7/1971 | Germany | 570/220 |
| 187 692 | 1/1988 | Hungary . | |
| 1146706 | 3/1969 | United Kingdom | 570/220 |

OTHER PUBLICATIONS

Derwent WPI Abstract: HU 30580 T—corresp. to CA101:18 of Oct. 29, 1984.

*Primary Examiner*—Alan Siegel
*Attorney, Agent, or Firm*—Millen, White, Zelano & Branigan, P.C.

[57] ABSTRACT

Ethylene is chlorinated in a reaction zone to form a product stream containing 1,2-dichloroethane, the latter being then thermally cracked in a cracking zone to form vinyl chloride. Light by-products formed during the thermal cracking step are chlorinated in a zone external and directly downstream of the reaction zone used for the preparation of the 1,2-dichloroethane product stream. The product stream leaving the chlorination reaction zone for the 1,2-dichloroethane are passed into said downstream zone so that the light by-products are chlorinated in the presence of said product stream.

10 Claims, No Drawings

PROCESS FOR CONVERTING THE LOW-BOILING BY-PRODUCTS FORMED DURING THE THERMAL CRACKING OF 1,2-DICHLOROETHANE

BACKGROUND OF THE INVENTION

The present invention relates to a process for converting secondary products formed during the thermal cracking of 1,2-dichloroethane in the preparation of vinyl chloride.

The current industrial processes for preparing vinyl chloride are based on the thermal cracking of 1,2-dichloroethane. Generally, 1,2-dichloroethane is obtained, either by liquid-phase chlorination of ethylene or by gas-phase oxychlorination of ethylene using a gas containing oxygen and derived from the thermal cracking of 1,2-dichloroethane and/or from any other source. The thermal cracking of 1,2-dichloroethane (referred to hereinbelow as DCE) is generally carried out at temperatures ranging from 300° C. to 650° C. and at pressures of between 8 bar and 40 bar.

A certain number of by-products liable to be found in DCE from cracking originate either from the products of the thermal dissociation, which are recycled, or from products resulting from the manufacture of the DCE.

The by-products are of a nature to give rise in particular to coking of the cracking oven faster than in the case of pure DCE. This coking results in an increase in the loss of charge in the reaction zone. Consequently, the production must be stopped frequently and this zone cleaned. Moreover, the presence of coke on the walls of the reactor results in an increase in temperature which may be detrimental to the strength of the equipment.

These by-products are classified herein as light byproducts and heavy by-products.

The term light by-products, referred to hereinbelow as the lights, is understood in the present text to denote products having a boiling point below 83.7° C., and the term heavy by-products, referred to hereinbelow as the heavies, is understood in the present text to denote products having a boiling point above 83.7° C.

Among the lights, mention will be made of saturated and unsaturated, optionally chlorinated aliphatic hydrocarbons such as 1,3-butadiene, acetylene, 2-chloro-1,3-butadiene, chloroprene, 1,1-dichloroethylene (trans), 1,1-dichloroethane, vinylidene chloride, chloroform, carbon tetrachloride and 1,1,2-trichloroethylene. Aromatic hydrocarbons such as benzene may also be detected.

Certain lights are difficult to separate from the unconverted DCE since their boiling points are very close to the boiling point of DCE (b.p.$_{760}$=83.7° C.) or alternatively because thay form azeotropes with the DCE. This is the case in particular for 1,1,2-trichloroethylene, which is virtually inseparable from DCE by standard distillation means.

In general, the products obtained from the thermal cracking are separated by successive distillations.

Thus, hydrogen chloride which may be used for the oxychlorination of ethylene, is recovered at the head of a first column. Vinyl chloride is recovered at the head of a second column.

Lights are recovered at the head of a third column and heavies and a large amount of DCE are recovered at the foot of the third column.

In general, the heavies undergo a further distillation which makes it possible to recover the unconverted DCE which is of sufficient purity to introduce it into the thermal cracking zone.

As regards the lights, many processes are known for removing them from the unconverted DCE.

Thus, according to British patent GB 938,824, the dissociation products, consisting of vinyl chloride hydrogen chloride, unconverted DCE and by-products, are quenched, HCl and the vinyl chloride are separated out by distillation as mentioned above and the lights, which are necessarily mixed with some of the unconverted DCE, are then subjected to elimination by distillation at the head of a column referred to as the column for fractionating the low-boiling products, and the distillation product is discarded. The main amount of the unconverted DCE is eliminated by distillation in a column for fractionating high-boiling products in order to separate out the high-boiling product. The disadvantage of this process is that the low-boiling products can only be eliminated from the cycle at the expense of large losses of DCE.

According to a process described in patent FR 2,038,347, the lights are converted into high-boiling products, that is to say above 83.7° C., and the pure DCE is extracted by distillation from the high-boiling products. This process is characterized in that the impure DCE is charged with chlorine gas, in the presence of catalysts which are common for the chlorination of ethylene to DCE, at temperatures between 30° C. and 85° C. Preferably, the process is performed in the presence of 50 to 500 ppm of $FeCl_3$, relative to the DCE, as catalyst. It is possible to proceed such that the impure DCE is conveyed to a plant used for the reaction of chlorine and ethylene with formation of DCE. The ethylene chlorine and the impure DCE are charged therein together in the presence of the catalyst. The catalyst is separated out by washing with water and the pure dichloroethane is eliminated by distillation from the high-boiling impurities.

According to a second variant, the process may be carried out so that the impure DCE is liberated, by distillation, from the low-boiling products. The total or partial amount of the concentrate of low-boiling products accumulating at the head of the column for fractionating the low-boiling products in question is removed continuously. The concentrate is charged with chlorine gas in the presence of the catalyst and the mixture containing the catalyst is conveyed to the column for fractionating the low-boiling products. The product at the bottom of the column for fractionating the low-boiling products is transferred continuously into a column for fractionating the high-boiling products and the pure DCE is removed by distillation from the high-boiling products containing the catalyst.

In a third variant, the process may be performed so that the impure DCE is liberated, by distillation, from the low-boiling products, the total amount or some of the concentrate of the low-boiling product accumulated at the head of the distillation column is removed continuously, and the concentrate is charged with chlorine gas in the presence of the catalyst. In the third variant, the mixture containing the catalyst is conveyed to the lower part of the column, the pure DCE below the head of the column is removed continuously and the high-boiling products are discharged from the bottom of the column.

Although effective for lowering the contents of certain by-products, these various techniques do, however, have certain drawbacks.

The fact that the lights are introduced into the zone for the preparation of the DCE by direct chlorination of ethylene makes it necessary to work with a large excess of chlorine, thereby entailing expensive subsequent treatments in order to destroy the unconsumed chlorine.

Moreover, the chlorination of the lights in the reactor for the chlorination of ethylene results in a considerable loss of selectivity for the reaction

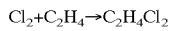

which is characterized by a very substantial increase in the formation of 1,1,2-trichloroethane.

The chlorination of the lights as proposed in the above-mentioned variants 2 and 3 requires additional apparatus, intricate implementation for effectively controlling the chlorination reactions, and the introduction of catalyst which will need to be purged thereafter.

SUMMARY OF THE INVENTION

A process has now been found for converting the light by-products formed during the thermal cracking of 1,2-dichloroethane (DCE), said process being characterized in that chlorination of the light by-products is carried out directly after preparation of the 1,2-dichloroethane by direct chlorination of ethylene, in the presence of the products resulting from the preparation of the 1,2-dichloroethane. According to the present invention, the products resulting from the preparation of the DCE mainly comprise DCE, catalyst and chlorine.

The chlorination of the lights, is generally conducted at a temperature of between 20° C. and 80° C., preferably between 50° C. and 70° C.

According to the present invention, the reaction for the chlorination of the lights is advantageously carried out continuously in a homogeneous reaction zone, downstream of the reactor for the direct chlorination of ethylene, into which zone the products resulting from the direct chlorination of ethylene, chlorine and said lights to be converted are introduced continuously.

The process is performed in the absence of any light radiation.

The products resulting from the direct chlorination of ethylene contain a weight amount of chlorine which may be up to 20,000 ppm or even more, and which is preferably between 300 ppm and 5000 ppm.

According to the present invention, the catalyst present in the products resulting from the preparation of the DCE by direct chlorination of ethylene is any conventional catalyst, preferably a Lewis acid such as, for example, ferric chloride.

According to the present invention, the content of catalyst in the products resulting from the preparation of the DCE is generally between 20 ppm and 200 ppm, and preferably between 30 ppm and 80 ppm.

It would not be departing from the scope of the invention if a catalyst as defined above was additionally introduced into the zone for converting the lights.

According to the present invention, the chlorine which is introduced, preferably in the molecular state, dissolves in the reaction medium and its concentration is advantageously maintained between 100 mg/kg and 2000 mg/kg of product leaving the zone for the chlorination reaction of the lights, and preferably at a concentration of between 200 mg/kg and 500 mg/kg.

According to the present invention, the residence time is sufficient to conduct the reaction of the lights, and is generally at least equal to 10 minutes and preferably between 20 minutes and 40 minutes.

The molecular chlorine used according to the present invention may be either in liquid form which is converted into gas before it is reacted, or in the form of chlorine gas in the crude state, as collected at the outlet of units for manufacturing chlorine by electrolysis of aqueous sodium chloride solutions. Thus, there is virtually no difference in employing liquid chlorine of 99.9% purity or a chlorine of 95% purity, the main impurities consisting of $CO_2$, $O_2$, $N_2$, $H_2$ and CO. These gaseous impurities are inert under the operating conditions of the reaction. The chlorine used may also be diluted with inert gases such as, for example, the gases which have just been mentioned. Such a dilution in a diluent/chlorine molar ratio which may be up to 1:1 does not harm the reaction.

According to the present invention, the lights are advantageously chlorinated in existing apparatus such as a buffer tank downstream of the said direct chlorination reactor, which tank is part of the direct chlorination unit.

The products leaving the zone for chlorination of the lights according to the present invention advantageously undergo two scrubbing stages, the first with water and the second with an alkaline solution, and they are then subjected to fractional distillation which allows the DCE to be separated from the chlorinated lights and from the impurities obtained from the reaction for the direct chlorination of ethylene. The DCE thus obtained is of a sufficient purity to be sent to the thermal cracking stage.

The process according to the invention results in a smaller consumption of chlorine as well as the use of a smaller amount of alkaline solution.

Furthermore, the process according to the present invention makes it possible to retain good selectivity in the reaction for the direct chlorination of ethylene.

It is also noted that the reaction for chlorination of the lights according to the present invention requires no additional equipment since it is carried out in the unit for the direct chlorination of ethylene.

Without further elaboration, it is believed that one skilled in the art can, using the preceding description, utilize the present invention to its fullest extent. The following preferred specific embodiment is, therefore, to be construed as merely illustrative, and not limitative of the remainder of the disclosure in any way whatsoever.

In the foregoing and in the following example, all temperatures are set forth uncorrected in degrees Celsius and unless otherwise indicated, all parts and percentages are by weight.

The entire disclosure of all applications, patents and publications, cited above and below, and of corresponding French application 96/03208, are hereby incorporated by reference.

EXAMPLE

The reaction for the chlorination of ethylene is carried out in an ordinary steel reactor equipped with a temperature-control system to keep the temperature inside the reactor constant.

The stream of products which leaves this reactor has the following characteristics:

| | |
|---|---|
| flow rate: | 38.5 t/h |
| temperature: | 62° C. |
| atmospheric pressure | |

|  |  |
|---|---|
| chlorine: | 1000 ppm |
| ferric chloride: | 30 ppm (expressed as iron) |
| purity of the 1,2-dichloroethane: | 99.8% (by weight) |

This stream of product flows into a buffer tank which also collects the DCE derived from condensation of the vent gases derived from the direct chlorination.

The lights obtained from the thermal cracking section of the DCE and separated out at the column for fractionating the high-boiling products are introduced at the same level as the above stream.

This stream of lights has the following characteristics:

|  |  |
|---|---|
| flow rate: | 2300 kg/h |
| weight composition: |  |
| DCE: | 90% |
| lights: | 10% |

The lights consist in particular of: benzene, vinyl chloride, vinylidene chloride, transdichloroethylene, chloroprene, 2-chloro-1,3-butadiene, 1,1,2-trichloroethylene, chloroform, carbon tetrachloride.

The residence time in the buffer tank is 20 minutes and the temperature is in the region of 60° C.

Chlorine is supplied in order to maintain a 300 ppm excess of chlorine in the exiting product.

The products leaving the buffer tank are scrubbed with water and then with a sodium hydroxide solution, and are subsequently subjected to fractional distillation.

200 kg/h of heavy impurities are recovered, which have consumed in total 120 kg/h of chlorine, of which about 30 kg/h is derived from the stream leaving the direct chlorination reactor and 90 kg/h is derived from the chlorine supplied.

The stream leaving the buffer tank no longer contains, in particular, any benzene, vinyl/chloride or chloroprene.

The preceding example can be repeated with similar success by substituting the generically or specifically described reactants and/or operating conditions of this invention for those used in the preceding example.

No degradation of the quality of the DCE formed in the direct chlorination reactor is observed, whereas the chlorination of the lights in the reactor for direct chlorination of ethylene results in particular in the degradation of a weight amount of DCE equal to 6000 ppm.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A process for converting light by-products having a boiling point below 83.7° C. formed during the thermal cracking of 1,2-dichloroethane (DCE), said process being characterized in that chlorination of the said light by-products is carried out directly after preparation of the 1,2-dichloroethane by direct chlorination of ethylene in a reaction zone, in the presence of 1,2-dichloroethane, catalyst and chlorine resulting from the preparation of the 1,2-dichloroethane without heavy by-products having a boiling point above 83.7° C., at a temperature of between 20° C. and 80° C., and in a zone external of said reaction zone.

2. A process according to claim 1, wherein the temperature is between 50° C. and 70° C.

3. A process according to claim 1, wherein the chlorination is carried out with molecular chlorine.

4. A process according to claim 3, wherein the concentration of molecular chlorine is maintained such that between 100 mg/kg the and 2000 mg/kg chlorine is present in the product leaving the external zone for the chlorination reaction of the lights.

5. A process according to claim 4, wherein the concentration of molecular chlorine is between 200 mg/kg and 500 mg/kg.

6. A process according to claim 1, wherein the residence time in the external zone is at least equal to 10 minutes.

7. A process according to claim 6, wherein the residence time is between 20 minutes and 40 minutes.

8. A process according to claim 1, wherein catalyst in the products resulting from the preparation of the 1,2-dichloroethane comprises ferric chloride.

9. A process according to claim 1, wherein the content of catalyst in the products resulting from the preparation of the 1,2-dichloroethane is between 20 ppm and 200 ppm.

10. In a process for producing vinyl chloride comprising:

(A) preparing 1,2-dichloroethane by direct chlorination of ethylene in a reactor;

(B) passing the resultant 1,2-dichloroethane product stream from said reactor directly to a downstream vessel;

(C) cracking said 1,2-dichloroethane to obtain vinyl chloride and light by-products boiling below 83.7° C.;

(D) passing said light by-products into said downstream vessel; and (E) chlorinating said light by-products in said downstream vessel in the presence of said 1,2-dichloroethane product stream without heavy by-products having a boiling point above 83.7° C.

* * * * *